United States Patent [19]

Jacobs et al.

[11] 4,260,559

[45] Apr. 7, 1981

[54] PREPARATION OF AMIDOSULFONIC ACIDS

[75] Inventors: Peter Jacobs, Frankenthal; Dietrich Mangold, Neckargemuend; Gerhard Hamprecht, Weinheim, all of Fed. Rep. of Germany

[73] Assignee: BASF Aktiengesellschaft, Fed. Rep. of Germany

[21] Appl. No.: 97,211

[22] Filed: Nov. 26, 1979

[30] Foreign Application Priority Data

Dec. 2, 1978 [DE] Fed. Rep. of Germany ....... 2852159

[51] Int. Cl.[3] ........................................ C07C 143/86
[52] U.S. Cl. ................................................ 260/513.6
[58] Field of Search ...................................... 260/513.6

[56] References Cited

U.S. PATENT DOCUMENTS

| | | | |
|---|---|---|---|
| 3,041,336 | 6/1962 | Teufel | 260/243 |
| 3,555,081 | 1/1971 | Zirner et al. | 260/513.6 |
| 3,708,277 | 1/1973 | Zeidler et al. | 71/91 |
| 3,822,257 | 7/1974 | Hamprecht et al. | 260/243 |
| 3,872,167 | 3/1975 | Hamprecht et al. | 562/430 |
| 3,883,509 | 5/1975 | Fischer et al. | 260/239 B |

FOREIGN PATENT DOCUMENTS

| | | | |
|---|---|---|---|
| 636329 | 9/1936 | Fed. Rep. of Germany | 260/513.6 |
| 1242627 | 12/1967 | Fed. Rep. of Germany | 260/543 |
| 1185439 | 3/1970 | United Kingdom | 260/513.6 |
| 1496174 | 12/1977 | United Kingdom | 260/513.6 |

OTHER PUBLICATIONS

Bieber, JACS, 75, 1405, 1409, (1953).
Ullmans Encyklopädie der Technischen Chemie, vol. 15, (1964), pp. 465–467.
Houben-Weyl, Methoden der Organischen Chemie, vol. VI/2, (1963), pp. 455–457.
Ibid, vol. IX, (1955), pp. 503–508.
Ibid, vol. XI/2, (1958), pp. 654–655.

*Primary Examiner*—Nicky Chan
*Attorney, Agent, or Firm*—Keil & Witherspoon

[57] ABSTRACT

Amidosulfonic acids are prepared by reacting ureas with oleum of a particular composition, first at a low temperature and then at a higher temperature, in the presence of an organic solvent. The products are starting materials for the preparation of dyes and pesticides.

7 Claims, No Drawings

PREPARATION OF AMIDOSULFONIC ACIDS

The present invention relates to a novel process for the preparation of amidosulfonic acids by reacting ureas with oleum of a particular composition, first at a low temperature and then at a higher temperature, in the presence of an organic solvent.

Houben-Weyl, Methoden der Organischen Chemie, Volume 11/2, pages 654–655, discloses that N,N'-dialkylureas can be first sulfonated, and then cleaved to give amidosulfonic acids, by treatment with oleum. It points out that the cleavage of the urea occurs at only a slightly higher temperature than the sulfonation, and specifies that the reaction should be carried out under very mild conditions to avoid a cleavage of, for example, an alkylurea prior to sulfonation, which would result in the formation of, for example, an alkylammonium bisulfate. As is shown by the Example given, relating to the preparation of methylsulfamic acid, the reaction temperature is from 0° C. to at most 45° C. An organic solvent is not present during the reaction; a large excess of 30% strength oleum is used. The isolation of the pure amidosulfonic acid requires involved purification operations, using ether.

German Pat. No. 636,329 concerns the same reaction with 35% strength oleum and mentions an after-treatment with sulfuric acid or water, without describing these embodiments in more detail. It is true that it mentions that the reaction can be completed by heating on a water bath, but it neither describes a two-stage process using different temperature ranges, nor recognizes in any way that the use of two stages is a critical factor. An organic solvent is not used in the process described.

A publication in J. Amer. Chem. Soc., 75 (1953), 1408 also concerns the reaction with oleum, without additional after-treatment, described in Houben-Weyl; it expressly mentions the difficulty of conducting the reaction to achieve an optimum yield, and in particular so as to suppress or reduce the formation of alkylammonium sulfate. The time at which the starting materials are added, and the temperature control of the reaction, are shown to be important. When working up, the end product must be washed repeatedly with ether, but in spite of these purification operations still contains sulfate and can only be purified by dissolving in methanol and precipitating by means of substantial amounts of ether. The reaction temperature is stated to be below 45° C. and it is pointed out that if cooling is inadequate (the Example refers to cooling with ice), the purity and yield of end product decrease substantially. 30% strength oleum, in excess, is used as the sole reagent.

British Pat. No. 1,185,439 draws attention to the disadvantage of using sulfuric acid, even in the form of oleum, since it always results in a highly impure end product, and the removal of the sulfuric acid is involved and difficult. The said British Patent therefore proposes a method in which the substituted urea is reacted with at least twice the equimolar amount of sulfur trioxide in the presence of an organic solvent. It points out that usually from 2 to 4, preferably 3, moles of sulfur trioxide are used per mole of urea. The reaction can also be carried out in two stages, in which case sulfur trioxide must be added to the reaction mixture in each stage. The yields are unsatisfactory. A substantial disadvantage of this process is that sulfur trioxide is very difficult to handle industrially.

U.S. Pat. No. 3,555,081 describes the same method for the synthesis of N-cyclohexylamidosulfonic acid and also shows that the use of sulfuric acid gives contaminated end products. It teaches (column 3, lines 45–54) that the absence of sulfuric acid in the reaction mixture is a critical factor. In two-stage methods, sulfuric acid should only be used together with sulfur trioxide, namely in the form of oleum, in the second reaction step.

German Laid-Open Application DOS 2,424,371 describes a two-stage process in which a substituted urea, in an organic solvent, is reacted, in a first step, with from 1 to 1.9 moles of sulfur trioxide per mole of starting material, and the resulting reaction mixture is reacted, in a second step, with from 1 to 1.5 moles of sulfuric acid per mole of starting material. It expressly points out that materials which contain sulfuric acid, eg. oleum, cannot be used in place of sulfur trioxide. A substantial disadvantage of this process is that sulfur trioxide is very difficult and expensive to handle industrially. In industrial operation, sulfur trioxide must as a rule be obtained from oleum by distillation in an additional apparatus, or be expelled slowly from oleum in special vessels by means of an inert gas, eg. carbon dioxide or nitrogen, or be obtained from the production of sulfuric acid via heated pipelines or in expensive special vessels. The said German Laid-Open Application expressly shows that the processes mentioned above, which use oleum from the start, or in the first stage, give substantially poorer yields.

All these processes are unsatisfactory in respect of optimum yield and purity of the end product coupled with simple, safe and economical operation, particularly on an industrial scale.

We have found that an amidosulfonic acid of the formula

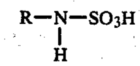

I where R is an aliphatic or cycloaliphatic radical, is obtained in an advantageous manner by reacting a urea with oleum in the presence of an organic solvent, if a substituted urea of the formula

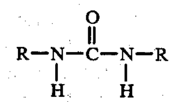

II where R has the above meaning, is reacted with oleum, which contains from 1 to 2.5 moles of sulfur trioxide and from 1 to 1.5 moles of sulfuric acid per mole of starting material II, in a first step at from −20° to +50° C., and then in a second step at from 50° C. to 140° C.

Where N,N'-dimethylurea is used, the reaction can be represented by the equation:

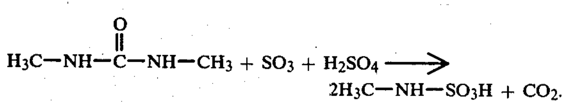

Compared to the first of the prior art processes mentioned, the process according to the invention gives amidosulfonic acids in better yield and greater purity, and by a simpler and more economical method. The process is carried out as a one-vessel process, in two stages. It is an essential feature of the invention that neither sulfur trioxide nor oleum is added in the second stage and that only oleum is used in the first stage. Compared to the process described in German Laid-Open Application DOS 2,424,371, the process according to the invention is simpler, safer and more economical; the handling of substantial amounts of sulfur trioxide, and the operation of appropriate special equipment are not needed. All these advantageous results of the process according to the invention are surprising in view of the prior art.

Preferred starting materials II and accordingly preferred end products I are those where R is alkyl of 1 to 12, preferably 1 to 5, carbon atoms or cyclohexyl. The above radicals may in addition be substituted by groups which are inert under the reaction conditions, eg. alkyl of 1 to 4 carbon atoms.

The following ureas are examples of suitable starting materials II: N,N'-dimethylurea, N,N'-diisopropylurea, N,N'-di-n-butylurea, N,N'-didodecylurea, N,N'-di-sec.-butylurea, N,N'-di-tert.-butylurea, N,N'-diethylurea, N,N'-dicyclohexylurea and N,N'-di-n-propylurea.

The first step of the reaction, and hence the entire reaction, is carried out with from 1 to 2.5 moles, preferably from 1 to 1.5 moles, especially from 1 to 1.1 moles, of sulfur trioxide and with from 1 to 1.5 moles, preferably from 1 to 1.2 moles, especially from 1 to 1.1 moles, of sulfuric acid per mole of starting material II. The preferred ratio is about 1 mole of sulfur trioxide per mole of $H_2SO_4$, the differences from the stoichiometric ratio advantageously being less than 10 percent by weight. In particular, the use of 45 percent strength by weight oleum (pyrosulfuric acid $H_2S_2O_7$) in the above ratios, more especially the use of from 178 to 195 percent by weight of oleum per mole of starting material II, is preferred. In place of oleum, advantageously 45 percent strength by weight oleum, mixtures of more concentrated oleum and/or sulfur trioxide with less concentrated oleum, sulfuric acid and/or water may be used, the mixtures being such as to correspond to an oleum containing the amounts of sulfur trioxide and amounts of sulfuric acid required according to the invention. The sulfuric acid used to form the oleum is as a rule 100% strength sulfuric acid (ie. sulfur trioxide monohydrate); if desired, aqueous sulfuric acid of down to 96 percent strength by weight may also be used to form the oleum. The sulfur trioxide used to form the oleum may be employed as a solid or advantageously as a liquid or as a gas; it is advantageously of 100 percent strength, but may also be diluted with an inert gas, eg. carbon dioxide or nitrogen. However, compounds which give sulfur trioxide under the conditions employed for mixing may also be used to form the oleum, for example adducts of sulfur trioxide, for instance with ethers, eg. tetrahydrofuran, di-($\beta$-chloroethyl) ether or 1,4-dioxane, with N,N-disubstituted carboxylic acid amides, eg. N,N-dimethylformamide, or with tertiary amines, eg. pyridine, triethylamine, trimethylamine, tributylamine, quinoline, quinaldine, dimethylaniline, triphenylamine, N-methylmorpholine, N-ethylmorpholine, N-methylpiperidine, N-ethylimidazole, N-methyleethyleneimine or N-ethylpentamethyleneimine, or adducts of chlorosulfonic acids with the above amines, especially with pyridine, or mixtures of the above adducts. Regarding the definition of 100 percent strength sulfur trioxide, reference may be made to Ullmanns Encyklopädie der technischen Chemie, Volume 15, pages 465–467, and regarding the preparation of adducts reference may be made to Houben-Weyl (loc. cit.), Volume VI/2, pages 455–457 and Volume IX, pages 503–508.

In a first step the reaction is carried out at from −20° C. to +50° C., advantageously from −10° C. to +30° C., preferably from −5° C. to +27° C., and in a second step at from above 50° C. to below 140° C., advantageously from 51° C. to 100° C., preferably from 51° C. to 85° C., under atmospheric or superatmospheric pressure, continuously or batchwise. In both steps, organic solvents which are inert under the reaction conditions are used, and advantageously the total amount of organic solvent is added at the time of the first reaction step. Examples of advantageous solvents are halohydrocarbons, especially chlorohydrocarbons, eg. tetrachloroethylene, amyl chloride, cyclohexyl chloride, dichloropropane, methylene chloride, dichlorobutane, chloroform, carbon tetrachloride, tetrachloroethane, trichloroethane, trichloroethylene, pentachloroethane, trichlorofluoromethane, cis-dichloroethylene, 1,2-dichloroethane, 1,1-dichloroethane, n-propyl chloride, 1,2-cis-dichloroethylene, n-butyl chloride, 2-, 3- and iso-butyl chloride and mixtures of the above. The solvent is advantageously used in an amount of from 200 to 10,000 percent by weight, preferably from 300 to 1,000 percent by weight, based on starting material II.

The reaction may be carried out as follows: a mixture of starting material II, solvent and oleum is kept at the reaction temperature of the first step for from 0.2 to 2 hours. Advantageously, the urea II is first suspended in a solvent and the oleum is introduced into the mixture with thorough mixing. Thereafter, in the second reaction step, the mixture is kept for from 0.2 to 5 hours at the reaction temperature appropriate to this step. The end product is then isolated from the reaction mixture in the conventional manner, for example by filtration. If the end product I is to be used further for industrial purposes, it is not absolutely essential to remove the solvent. The fact that the solvent used need not be removed is particularly advantageous when stoichiometric amounts of the reactants are used, since after the reaction the solvent only contains small amounts of impurities.

The compounds obtainable by the process of the invention are valuable starting materials for the preparation of dyes and pesticides. For example, they may be chlorinated, for example with thionyl chloride or phosphorus pentachloride, to give the corresponding amidosulfonic acid chlorides, for example methylaminosulfonyl chloride or isopropylaminosulfonyl chloride; from these, the o-sulfamidobenzoic acids described in German Published Application DAS 2,104,682 may be prepared by reaction with anthranilic acid or its salts. Cyclization of these compounds, for example by the process described in German Laid-Open Application DOS 2,105,687, gives the 2,1,3-benzothiadiazin-4-one-2,2-dioxides, the use of which for crop protection agents and drugs is described in the said DOS. Regarding the use of the compounds obtainable according to the invention, reference may be made to the above publications and to German Published Application DAS 1,120,456, German Pat. No. 1,242,627 and German Laid-Open Application DOS 1,542,836. The alkylamidosulfonyl chlorides obtainable from alkylamidosulfonic acids are valuable starting materials for the synthesis of the herbicidal O-(alkylaminosulfonyl)-glycolic acid amides (U.S. Pat. No. 3,883,509) by reaction with a substituted glycolic acid amide in the presence of an acid acceptor.

In the Examples which follow, parts are by weight and bear the same relation to parts by volume as that of the kilogram to the liter.

EXAMPLE 1

Methylamidosulfonic acid:

63 parts of N,N'-dimethylurea are suspended in 500 parts by volume of 1,2-dichloroethane. 96 parts of oleum (containing 65% by weight of $SO_3$) are added to the mixture at 25° C., followed by 36 parts of 100% strength by weight sulfuric acid. The total reaction time in the first step is 30 minutes. The reaction mixture is then heated to 70°-80° C. under reflux, whereupon methylamidosulfonic acid precipitates as crystals, and $CO_2$ is evolved. The total reaction time in the second step is 60 minutes. After the mixture has cooled, it is filtered and the filter residue is washed with 100 parts by volume of dichloroethane.

Yield: 162 parts (virtually quantitative) of methylamidosulfonic acid, of melting point 182.3° C.

EXAMPLE 2

Methylamidosulfonic acid:

224 parts of N,N'-dimethylurea are suspended in 1,500 parts by volume of 1,2-dichloroethane. 454 parts of 45 percent strength by weight oleum are added to the mixture at 25° C. and the batch is then stirred at this temperature for half an hour. The total reaction time in the first step is 45 minutes. The mixture is then heated at 70°-80° C. under reflux, whereupon methylamidosulfonic acid precipitates as crystals and $CO_2$ is evolved. The total reaction time in the second step is 60 minutes. After the mixture has cooled, it is filtered and the filter residue is washed with dichloroethane.

Yield: 565 parts (virtually quantitative) of methylamidosulfonic acid, of melting point 182.3° C.

EXAMPLE 3

Ethylamidosulfonic acid:

260 parts of N,N'-diethylurea are suspended in 1,500 parts by volume of 1,2-dichloroethane. 454 parts of 45 percent strength by weight oleum are added to the mixture at 25° C. and the batch is then stirred at this temperature for half an hour. The total reaction time in the first step is 45 minutes. The mixture is then heated at 70° C. under reflux, whereupon ethylamidosulfonic acid precipitates as crystals and $CO_2$ is evolved. The total reaction time in the second step is 60 minutes. After the mixture has cooled to room temperature, it is filtered and the filter residue is washed with dichloroethane.

Yield: 630 parts (virtually quantitative) of ethylamidosulfonic acid, of melting point 170° C. (with decomposition).

EXAMPLE 4

Isopropylamidosulfonic acid:

104 parts of N,N'-diisopropylurea are suspended in 500 parts by volume of 1,2-dichloroethane. 96 parts of 65 percent strength by weight oleum are added to the mixture at 0°-5° C. The batch is then stirred for half an hour at 5°-10° C., after which 39 parts of 100 percent strength by weight sulfuric acid are added at 25° C. The total reaction time in the first step is 45 minutes. The mixture is heated under reflux (80° C.) until the evolution of $CO_2$ has ended. The total reaction time in the second step is 120 minutes. After the mixture has cooled, it is filtered and the filter residue is washed with dichloroethane.

Yield: 195 parts (virtually quantitative) of isopropylamidosulfonic acid of melting point 167° C.

EXAMPLE 5

Isopropylamidosulfonic acid 104 parts of N,N'-diisopropylurea are suspended in 500 parts by volume of 1,2-dichloroethane. 139 parts of 45 percent strength by weight oleum are added to the mixture at −10° C., and the batch is then kept at from −4° C. to 0° C. for one hour. The total reaction time in the first step is 80 minutes. The mixture is then heated, whereupon evolution of $CO_2$ commences. Heating is continued, under reflux (80° C.), until the evolution of $CO_2$ has ended. The total reaction time in the second step is 120 minutes. When the mixture has cooled, it is filtered and the filter residue is washed with dichloroethane.

Yield: 191 parts (96% of theory) of isopropylamidosulfonic acid of melting point 167° C.

We claim:

1. A process for the preparation of an amidosulfonic acid of the formula

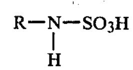
I where R is an aliphatic or cycloaliphatic radical, by reacting a urea with oleum in the presence of an organic solvent, wherein a substituted urea of the formula

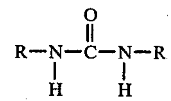
II where R has the above meaning, is reacted with oleum, which contains from 1 to 2.5 moles of sulfur trioxide and from 1 to 1.5 moles of sulfuric acid per mole of starting material II, in a first step at from −20° to +50° C., and then in a second step at from 50° C. to 140° C.

2. A process as claimed in claim 1, wherein the reaction is carried out with from 1 to 1.5 moles of sulfur trioxide per mole of starting material II.

3. A process as claimed in claim 1, wherein the reaction is carried out with from 1 to 1.2 moles of sulfuric acid.

4. A process as claimed in claim 1, wherein the reaction is carried out with 45 percent strength by weight oleum.

5. A process as claimed in claim 1, wherein the reaction is carried out in the first step at from −10° C. to +30° C.

6. A process as claimed in claim 1, wherein the reaction is carried out in the second step at from 51° C. to 100° C.

7. A process as claimed in claim 1, wherein the reaction is carried out with from 200 to 10,000 percent by weight, based on starting material II, of an organic solvent which is inert under the reaction conditions.

* * * * *